United States Patent

Francois et al.

[11] Patent Number: 5,854,246
[45] Date of Patent: Dec. 29, 1998

[54] TOPICAL KETOCONAZOLE EMULSIONS

[75] Inventors: Marc Karel Jozef Francois, Kalmthout; Eric Carolus Leonarda Snoeckx, Beerse, both of Belgium

[73] Assignee: Janssen Pharmaceutica, N.V., Beerse, Belgium

[21] Appl. No.: 793,359

[22] PCT Filed: Aug. 25, 1995

[86] PCT No.: PCT/EP95/03366

§ 371 Date: Feb. 24, 1997

§ 102(e) Date: Feb. 24, 1997

[87] PCT Pub. No.: WO96/06613

PCT Pub. Date: Mar. 7, 1996

[30] Foreign Application Priority Data

Sep. 1, 1994 [EP] European Pat. Off. ............ 94 202 505

[51] Int. Cl.$^6$ ................ A61K 31/495; A61K 31/50; A61K 31/215; A61K 47/00

[52] U.S. Cl. ............ 514/252; 514/852; 514/881; 252/106; 252/172; 252/174.11; 252/544; 252/547; 252/551; 252/555; 252/399

[58] Field of Search ............ 252/106, 173, 252/124.11, 124.23, 544, 547, 551, 555, 399; 514/257, 852, 881

[56] References Cited

U.S. PATENT DOCUMENTS

| | | | |
|---|---|---|---|
| 4,335,125 | 6/1982 | Heeres et al. | 424/250 |
| 4,942,162 | 7/1990 | Rosenberg et al. | 514/252 |
| 4,976,953 | 12/1990 | Orr et al. | 424/47 |
| 5,002,974 | 3/1991 | Geria | 514/782 |
| 5,215,839 | 6/1993 | Kamishita et al. | 424/45 |
| 5,456,851 | 10/1995 | Lin et al. | 252/106 |

*Primary Examiner*—Keith D. MacMillan
*Attorney, Agent, or Firm*—Mary Appollina

[57] ABSTRACT

The invention concerns stable emulsions comprising ketoconazole having a pH in the range from 6 to 8, characterized in that the emulsions lack sodium sulfite as an antioxidant; process of preparing said emulsions.

7 Claims, No Drawings

TOPICAL KETOCONAZOLE EMULSIONS

CROSS-REFERENCE TO RELATED APPLICATIONS

This application claims priority from PCT/EP95/03366, filed on Aug. 25, 1995, which in turn claimed priority from EP 94.202.505.7, filed on Sep. 1, 1994.

The subject invention furnishes stable ketoconazole emulsions for topical use lacking sodium sulfite, thus reducing the potential of skin irritation or sensitization by this agent. The subject compositions display a shelf life comparable with the art cream formula, but with a significant improvement in tolerability. Ketoconazole, the preparation thereof and its utility as an antifungal have been described in U.S. Pat. No. 4,335,125. A 2% ketoconazole dermal cream, containing ketoconazole, propylene glycol, 1-octadecanol, 1-hexadecanol, sorbitan monostearate, polysorbate 60, polysorbate 80, isopropyl myristate, sodium sulfite and water is commercially available since many years in several countries. Although this cream is efficacious in the treatment of mycotic infections of the skin, it was desired to improve the tolerability of the composition while maintaining a satisfactory shelf life. Ketoconazole is subject to degradation by oxidation. The art ketoconazole dermal cream was stabilized by sodium sulfite, which is a common antioxidant. Unexpectedly, it has been found that no significant degradation of ketoconazole was observed after omitting the antioxidant from the emulsion, if only the pH of the formula was maintained in a strict range.

In particular, the present invention concerns emulsions comprising ketoconazole and having a pH in the range from 6 to 8, characterized in that the emulsions lack sodium sulfite as an antioxidant.

The subject compositions should be applied topically, by covering the affected and immediately surrounding area The emulsions show the advantage that they allow a once-daily dosage schedule. It is evident that the dosage schedule may be altered depending on the response of the treated subject and/or depending on the evaluation of the physician prescribing the compositions of the instant invention.

The term "stable" as used herein relates to compositions wherein the decrease in the ketoconazole content is less than 10%, preferably less than 5% and most preferably less than 2%, after storage at 40° C. or below for up to 12 months.

Ketoconazole is the generic name of 1-acetyl-4-[4-[2-(2, 4-dichlorophenyl)-2-imidazol-1-ylmethyl-1,3-dioxolan-4-ylmethoxy]phenyl]piperazine. The term "ketoconazole" as used herein comprises ketoconazole in the free base form, the pharmaceutically acceptable addition salts, the stereochemically isomeric forms thereof and the tautomeric forms thereof. The preferred ketoconazole compound is the (±)-(cis) form of the free base form. The acid addition forms may be obtained by reaction of the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which ketoconazole as well as the salts thereof, are able to form. Such solvates are for example hydrates, alcoholates and the like.

Hereinafter, the amounts of each of the ingredients in the compositions are expressed as percentages by weight based on the total weight of the formulation. Similarly, ratios are intended to define weight-by-weight ratios.

The concentration of ketoconazole in the emulsions according to the invention may range from 0.1% to 10%, preferably from 0.5% to 5%, more preferably from 1% to 3% and in particular it is about 2%. Up to 99% or more of the ketoconazole may be in suspension in the emulsions, the remainder (if any) being dissolved.

The emulsions of the present invention consist of an aqueous phase and an oil phase. The compositions may take the form of a water-in-oil emulsion or, preferably, an oil-in-water emulsion. Suitably, the emulsions comprise from 50 to 80% water. The oil phase of the emulsion may comprise, for example, paraffin oil, fractionated coconut oil, isopropyl myristate; fatty alcohols such as cetyl (hexadecanol), stearyl alcohol (octadecanol) and the like; fatty acid esters such as sorbitan monostearate and the like.

The emulsions may be applied in the form of conventional products such as creams, emulsion gels, lotions and the like. The formulations can be packaged in suitable, art-known containers such as plastic, glass or ceramic pots, tubes, e.g. PVC-covered aluminum tubes or bottles with a spraying device.

A first group of emulsions takes the form of a cream formulation (type I). The oil phase of these cream formulae preferably comprises isopropyl myristate as its presence results in a favourable viscosity and spreadability of the cream, which improve the cosmetic acceptability of the product.

Certain skin types (e.g. greasy skin) and disease states, however, require formulations with a low content of fatty materials. Formulations with a limited greasiness also show the advantage in that they are more easily applicable to haired skin. A second group of emulsions therefor takes the form of an emulsion gel (type II). These emulsions of type II contain only a minor amount of fatty materials. Fatty materials as used herein comprise the oil phase substances mentioned hereinabove as well as, for example, fatty acids such as stearic acid, palmitic acid, myristic acid, and the like. Preferably, the concentration of the fatty materials in the type II emulsions is from 1 to 10%, more preferably is about 5%. Type II emulsions suitably comprise fractionated coconut oil as the oil phase.

The subject emulsions may further comprise various additives such as emulsifiers, buffer systems, wetting agents, acids or bases, stabilizing agents, antimicrobial preservatives, thickening agents and the like. Suitable emulsifiers are, for example, anionic, cationic or, more preferably, nonionic emulsifiers, such as, for example, sucrose esters; glucose esters; polyoxyethylated fatty esters; polyoxyethylated fatty alcohol ethers; glycerol esters, e.g. glycerol monostearate; sorbitan esters, e.g. sorbitan monopalmitate (=Span 40®), sorbitan monostearate (=–Span 60®); polyoxyethylene derivatives of sorbitan esters, e.g. polysorbate 40 (=–Tween 40®), polysorbate 60 (=Tween 60®), cetyl dimethicon copolyol and the like. The cream compositions of type I preferably comprise as emulsifying constituents sorbitan monostearate and polysorbate 60 in an amount of 0.5 to 10% each, preferably in an amount of 1 to 2% each. Examples of appropriate wetting agents are polyoxyethylene derivatives of sorbitan esters, e.g. polysorbate 80 (=Tween 80®), polysorbate 20 (=Tween 20®), sodium lauryl sulfate, sodium dioctyl sulfosuccinate, and the like. Preferably, polysorbate 80 is used in an amount from 0.01 to 1%, preferably in an amount from 0.1 to 0.2%. Buffer systems comprise mixtures of appropriate amounts of an acid such as phosphoric, succinic, tartaric, lactic, or citric acid, and a base, in particular sodium hydroxide or disodium hydrogen phosphate. Alternatively, the pH of the composition can be fixed upon addition of an acid such as hydrochloric acid or a base such as sodium hydroxide and the like. Acids and/or bases are included in the emulsion to maintain the pH of the formulation in the range from 6 to 8, more preferably in the range from 6.5 to 7.5, most preferably at about 7.

Suitable stabilizing agents which improve the physico-chemical stability of the composition are for example inorganic salts, e.g. sodium chloride and the like, propylene glycol, glycerin, and the like. Propylene glycol may also be included in the formulation as an humectant. Preferably, the emulsions comprise 10% or less propylene glycol in order to further reduce the potential of irritation and sensitization. Suitably, the emulsions comprise from 0.5 to 10%, preferably from 5 to 10% of propylene glycol. In a particular aspect of the invention, the emulsions comprise an antimicrobial preservative, in particular two or more antimicrobial preservatives. When using a combination of preservatives, the quantities of these preservatives can be reduced as compared to the use of a single preservative, while retaining compliance with the requirements on microbial counts stipulated by the Pharmacopoeia. Decreasing the concentration of the preservatives reduces the potential of irritation and sensitization. Suitable preservatives in the subject compositions are the antimicrobial acids and their salts, e.g. benzoic acid and its salts, sorbic acid and its salts, propionic acid and its salts; formaldehyde and formaldehyde donors, e.g. bronopol, glutaric dialdehyde, methyloldimethyl hydantoin (MDMH), dimethyloldimethyl hydantoin (DMDMH), quaternium 15 (=Dowicil 200®), diazolidinyl urea (=Germal II®) and imidazolidinyl urea (=Germal 115®); the mercury salts, e.g. phenylmercuric acetate, phenylmercuric borate, phenylmercuric nitrate and thiomersal; EDTA and its salts, e.g. sodium EDTA; ethanol; cresol and the derivatives thereof, e.g. chlorocresol and isopropyl cresol; benzyl alcohol; dichloro benzylalcohol (=Myacide SP®); hexamidine isethionate; hexetidine; the quaternary compounds, e.g. cetrimide, benzalkonium chloride and the like; the parabens, e.g. methyl paraben and propyl paraben; chlorhexidine and the salts thereof. Suitably, imidazolidinyl urea, cetrimide, sodium EDTA and/or diazolidinyl urea are employed in the emulsions. The concentration of each preservative preferably does not exceed 0.5%, more preferably does not exceed 0.3%. The viscosity of the subject formulations may be increased upon the addition of thickening agents, such as, for example lyophobic agents such as, for example, 1-octadecanol, 1-hexadecanol, glycerol monostearate, Carnauba wax, beeswax, trihydroxystearate and the like; or lyophilic agents such as, for example, cellulose derivatives, e.g. sodium carboxymethylcellulose; polyethylene oxide; chitin and the derivatives thereof, e.g. chitosan; poloxamers; clays; natural gums; starch derivatives; carbomers (polyacrylic acid derivatives); polyethylene glycol; and the like. Suitable emulsions of type I comprise as thickening agents 1-octadecanol and 1-hexadecanol in an amount of 0.5 to 10% each, preferably in an amount of approximately 7.5% and 2%, respectively. Emulsion gels of type II suitably comprise a carbomer thickener in an amount from 0.1 to 5%, preferably in an amount from 0.3 to 0.6%. The emulsion gels of type II comprising a carbomer thickener display a favourable spreadability on the skin by a very quick drop in viscosity during rubbing in ("quick breaking" effect). The latter characteristic is particularly useful when applied to haired or inflammated skin or large body surfaces. When using a carbomer thickener in the present emulsions, little or no emulsifying substances are required to obtain stable formulations. Particular emulsions of type II further comprise a polyethylene oxide thickener in an amount from 0.1 to 1%, preferably in amount of approximately 0.2%. Preferably, the polyethylene oxide thickener has an average molecular weight of 200000. The use of polyethylene oxide in the emulsion gels has cosmetic advantages in that a soft feeling is experienced during rubbing in.

Preferred emulsions comprise by weight based on the total weight of the composition:
(a) 0.5 to 5% ketoconazole;
(b) buffer, acid or base to maintain the pH of the composition in the range from 6 to 8;
(c) sufficient dermatologically acceptable antimicrobial preservatives to prevent degradation of the composition;
(d) 0.5 to 40% of a dermatologically acceptable oil; and
(e) water ad 100%.

More preferred emulsions are those preferred emulsions further comprising a thickening agent and a wetting agent.

A preferred emulsion of type I (cream formula) comprises by weight based on the total weight of the composition:
(a) 0.5% to 5% ketoconazole;
(b) buffer, acid or base to maintain the pH in the range from 6 to 8;
(c) 0.1% to 0.5% diazolidinyl urea and 0.1% to 0.5% sodium EDTA;
(d) 0.5% to 5% isopropyl myristate;
(e) 5% to 10% 1-octadecanol and 1% to 5% 1-hexadecanol;
(f) 0.5% to 5% sorbitan monostearate and 0.5% to 5% polysorbate 60;
(g) 5% to 10% propylene glycol;
(h) 0.05% to 0.2% polysorbate 80; and
(i) water ad 100%.

The most preferred emulsions of type I (cream formula) comprise approximately by weight based on the total weight of the composition:
(a) 2% ketoconazole;
(b) buffer, acid or base to maintain the pH in the range from 6 to 8;
(c) 0.2% diazolidinyl urea and 0.1% sodium EDTA;
(d) 1% isopropyl myristate;
(e) 7.5% 1-octadecanol and 2% 1-hexadecanol;
(f) 2% sorbitan monostearate and 1.5% polysorbate 60;
(g) 10% propylene glycol;
(h) 0.1% polysorbate 80; and
(i) water ad 100%.

A preferred emulsion of type II (emulsion gel formula) comprises by weight based on the total weight of the composition:
(a) 0.5% to 5% ketoconazole;
(b) buffer, acid or base to maintain the pH in the range from 6 to 8;
(c) 0.1% to 0.5% imidazolidinyl urea, 0.1% to 0.5% cetrimide and 0.1% to 0.5% sodium EDTA;
(d) 1% to 10% fractionated coconut oil;
(e) 0.1% to 2% carbomer and 0.1% to 0.5% polyethylene oxide;
(f) 5% to 10% propylene glycol;

(g) 0.1% to 0.5% polysorbate 80; and (h) water ad 100%.

The most preferred emulsions of type II (emulsion gels) comprise approximately by weight based on the total weight of the composition:

(a) 2% ketoconazole;

(b) buffer, acid or base to maintain the pH in the range from 6 to 8;

(c) 0.3% imidazolidinyl urea, 0.1% cetrimide and 0.2% sodium EDTA;

(d) 5% fractionated coconut oil;

(e) 0.45% carbomer and 0.2% polyethylene oxide;

(f) 5% propylene glycol;

(g) 0.2% polysorbate 80; and (h) water ad 100%.

To prepare the pharmaceutical compositions of this invention, a therapeutically effective amount of ketoconazole is combined in intimate admixture with the dermatologically acceptable carrier following art-known procedures. Preferably, the carrier formulation is prepared separately and the active ingredients are then added thereto.

The preparation of the cream formulas of type I suitably comprises the following steps:

(1) the stabilizing agents and an emulsifier are dissolved in the water phase;

(2) the thickening agents and an emulsifier are dissolved in the oil phase;

(3) phases (1) and (2) are homogenized;

(4) the wetting agents and the preservatives are dissolved in water;

(5) ketoconazole is suspended in phase (4);

(6) phases (3) and (5) are mixed;

(7) buffer, acid or base is added to adjust the pH in the range from 6 to 8; and (8) phase (7) is diluted with water to the desired volume.

The preparation of the emulsion gels of type II suitably comprises the following steps:

(1) the thickening agents are suspended in the oil phase;

(2) the preservatives are dissolved in the water phase;

(3) phases (1) and (2) are mixed;

(4) buffer, acid or base is added to adjust the pH in the range from 6 to 8; and (5) ketoconazole is suspended in (4).

Optionally, the above procedure is conducted under an inert atmosphere, e.g. oxygen-free nitrogen or argon. Optionally, ketoconazole may be added to the carrier formulation by introduction of the powder into the container with the carrier formulation under vacuo. Further, it may be advantageous to use micronized forms of ketoconazole to increase the contact surface of the drug with the skin. Micronized forms can be prepared by micronization techniques known in the art, e.g. by milling in appropriate mills and sieving through appropriate sieves.

The following examples are intended to illustrate the scope of the present invention in all its aspects.

EXAMPLE 1

F1 (Emulsion Gel)

| Ingredient | Quantity |
| --- | --- |
| Ketoconazole microfine | 20 mg |
| Miglyol 812 (fractionated coconut oil) | 50 mg |
| Polyethylene oxide 200000 | 2 mg |
| Propylene glycol | 50 μl |
| Imidazolidinyl urea | 3 mg |
| Cetrimide | 1 mg |
| Sodium EDTA | 2 mg |
| Polysorbate 80 | 2 mg |
| Carbomer 1382 | 4,5 mg |
| Sodium Hydroxide p.a. | q.s. ad pH = 7 |
| Purified water | q.s. ad 1 g |

(1) 2 mg polyethylene oxide 200000 was suspended in 50 μl propylene glycol;

(2) 4.5 mg carbomer 1382 was suspended in 50 mg Miglyol 812;

(3) 1 mg cetrimide, 2 mg sodium EDTA and 2 mg Polysorbate 80 were dissolved in 0.85 g water;

(4) suspension (1) was added to solution (3);

(5) suspension (2) was added to solution (4);

(6) sodium hydroxide was added until pH=7;

(7) water was added to (6) until 1 g; and (8) 2 mg ketoconazole was suspended in (7).

EXAMPLE 2

F2 (Cream)

| Ingredient | Quantity, mg/g cream |
| --- | --- |
| Ketoconazole microfine | 20 mg |
| Diazolidinyl Urea | 2 mg |
| Sodium EDTA | 1 mg |
| Propylene glycol | 100 μl |
| 1-Octadecanol | 75 mg |
| 1-Hexadecanol | 20 mg |
| Sorbitan monostearate | 20 mg |
| Polysorbate 60 | 15 mg |
| Isopropyl myristate | 10 mg |
| Polysorbate 80 | 1 mg |
| Sodium Hydroxide | q.s. ad pH = 7 |
| Purified water | q.s. ad 1 g |

(1) 100 μl propylene glycol and 15 mg polysorbate 60 were dissolved in water upon stirring at 70°–75° C.;

(2) 10 mg isopropyl myristate, 75 mg 1-octadecanol, 20 mg 1-hexadecanol and 20 mg sorbitan monostearate were mixed at 75°–80° C.;

(3) phase (1) was homogenized with phase (2) upon stirring and cooled to 35°–40° C.;

(4) 1 mg polysorbate 80, 2 mg diazolidinyl urea and 1 mg sodium EDTA were dissolved in water upon stirring;

(5) 20 mg ketoconazole microfine was suspended in phase (4) upon stirring;

(6) phase (5) is mixed with phase (3) upon stirring;

(7) sodium hydroxide is added to phase (6) until pH=7 is reached; and (8) phase (7) is diluted with water to 1 g.

EXAMPLE 3

The emulsion F1 as described hereinabove was stored for 12 months at 4° C., 25° C., 30° C. and 40° C. The concentration of ketoconazole had not significantly changed after storage at neither of these temperatures. No degradation products were detected. Hence, the emulsion F1 is in compliance with the requirements of a stable formulation as set forth hereinabove.

We claim:

1. A stable and less irritating oil-in-water emulsion for topical application to the skin comprising by weight based on the total weight of the emulsion:
   (a) 0.5 to 5% ketoconazole microfine;
   (b) buffer, acid or base to maintain the pH of the emulsion in the range of from 6 to 8;
   (c) sufficient dermatologically acceptable antimicrobial preservatives to prevent degradation of the emulsion;
   (d) 0.5 to 10% of a stabilizing agent which is propylene glycol;
   (e) 0.5 to 40% of a dermatologically acceptable oil; and
   (f) water ad 100%;
provided that the emulsion lacks sodium sulfite as an antioxidant.

2. An emulsion according to claim 1 which takes the form of a cream formulation.

3. An emulsion according to claim 1 which takes the form of an emulsion gel and wherein the concentration of fatty materials ranges from 1% to 10% by weight.

4. An emulsion according to claim 1 comprising two or more antimicrobial preservatives selected from the group of imidazolidinyl urea, cetrimide, sodium EDTA and diazolidinyl urea.

5. An emulsion according to claim 1 which takes the form of a cream and which comprises by weight based on the total weight of the composition:
   (a) 0.5% to 5% ketoconazole microfine;
   (b) buffer, acid or base to maintain the pH in the range from 6 to 8;
   (c) 0.1% to 0.5% diazolidinyl urea and 0.1% to 0.5% sodium EDTA;
   (d) 0.5% to 5% isopropyl myristate;
   (e) 5% to 10% 1-octadecanol and 1% to 5% 1-hexadecanol;
   (f) 0.5% to 5% sorbitan monostearate and 0.5% to 5% polysorbate 60;
   (g) 5% to 10% propylene glycol;
   (h) 0.05% to 0.2% polysorbate 80; and
   (i) water ad 100%.

6. An emulsion according to claim 1 which takes the form of an emulsion gel and which comprises by weight based on the total weight of the composition:
   (a) 0.5% to 5% ketoconazole microfine;
   (b) buffer, acid or base to maintain the pH in the range from 6 to 8;
   (c) 0.1% to 0.5% imidazolidinyl urea, 0.1% to 0.5% cetrimide and 0.1% to 0.5% sodium EDTA;
   (d) 1% to 10% fractionated coconut oil;
   (e) 0.1% to 2% carbomer and 0.1% to 0.5% polyethylene oxide;
   (f) 5% to 10% propylene glycol;
   (g) 0.1% to 0.5% polysorbate 80; and
   (h) water ad 100%.

7. An emulsion according to claim 1, wherein the dermatologically acceptable oil is paraffin oil, fractionated coconut oil, isopropyl myristate, a fatty alcohol, a fatty acid ester or a fatty acid.

* * * * *